US006469957B1

(12) United States Patent
Savord et al.

(10) Patent No.: US 6,469,957 B1
(45) Date of Patent: Oct. 22, 2002

(54) ARBITRARY SIGNAL GENERATOR FOR DRIVING ULTRASONIC TRANSDUCERS

(75) Inventors: Timothy J Savord, Lowell, MA (US); Robert K. O'Toole, Chester, NH (US); Richard F Dillman, Andover, MA (US); Douglas Rosich, N. Reading, MA (US); Ronald Dennis Gatzke, Lexington, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 18 days.

(21) Appl. No.: 09/691,612

(22) Filed: Oct. 18, 2000

(51) Int. Cl.$^7$ ................................................ G03B 42/06
(52) U.S. Cl. ...................................................... 367/137
(58) Field of Search ................................. 367/138, 11, 7

(56) References Cited

U.S. PATENT DOCUMENTS

| 5,410,516 | A | | 4/1995 | Uhlendorf et al. |
| 5,608,690 | A | | 3/1997 | Hossack et al. |
| 5,675,554 | A | | 10/1997 | Cole et al. |
| 5,740,128 | A | | 4/1998 | Hossack et al. |
| 5,833,613 | A | | 11/1998 | Averkiou et al. |
| 6,222,795 | B1 | * | 4/2001 | Hossack et al. ............ 367/138 |
| 6,292,435 | B1 | * | 9/2001 | Savord et al. ............... 367/138 |

OTHER PUBLICATIONS

H.W. Persson, "Electric Excitation of Ultrasound Transducers for Short Pulse Generation", Ultrasound in Med. & Biol., vol. 7, pp. 285–291 (1981).

R.Y. Liu, "The Design of Electric Excitations for the Formation of Desired Temporal Responses of Highly Efficient Transducers", Acoustical Imaging, vol. 12, pp. 293–305 (1982).

J.A. Hossack, "Improving the Characteristics of a Transducer Using Multiple Piezoelectric layers," IEEE Transactions on Ultrasonics, Ferroelectrics, and Frequency Control, vol. 40, No. 2, pp. 131–139 (Mar. 1993).

* cited by examiner

Primary Examiner—Daniel T. Pihulic
(74) Attorney, Agent, or Firm—John Vodopia

(57) ABSTRACT

An arbitrary waveform generator includes an arithmetic element that can access samples from a waveform sample memory and adjust values accessed from the waveform sample memory to modify waveform power or amplitude. In an illustrative embodiment of the arbitrary waveform generator, the arithmetic element is a multiplying digital-to-analog converter (DAC) that has a first input connection for receiving digitized waveform samples and has a second input connection for receiving a reference signal. An output signal from the multiplying DAC is a mathematical product of the digitized waveform samples and the reference signal. In one example, a reference digital-to-analog converter (DAC) generates the reference signal. In some examples, the digitized waveform samples are digitized samples of an analog waveform signal. In some examples, the arithmetic element is incorporated into the arbitrary waveform generator in a manner to maintain transmit signal resolution over a full range of transmit power settings.

27 Claims, 3 Drawing Sheets

ARBITRARY SIGNAL GENERATOR FOR DRIVING ULTRASONIC TRANSDUCERS

BACKGROUND OF THE INVENTION

Ultrasound imaging systems, such as medical ultrasound systems, typically use a transducer comprised of a phased array of individually driven elements to generate interrogation signals. The most popular method, until recently, for driving ultrasonic transducer elements has been to apply timed electrical pulses to each element of the transducer. By properly adjusting the start time of the pulse for each transducer element, acoustic beams, that can be focused and steered, are formed. Images are created from the returned echoes of the acoustic beams as they are progressively swept across a target area.

Known pulse driving circuits for phased arrays transducer are described by Hans W. Persson in "Electric Excitation of Ultrasound Transducers for Short Pulse Generation," Ultrasound in Med. & Bio., Vol. 7, 1981. Such drive circuits are typically limited to generating rectangular waveforms that often exhibit exponentially decaying segments. The amplitude of drive signals created by pulse generator circuits is determined by the magnitude of a programmable d.c. voltage source. Programmable d.c. voltage source typically do not have the agility to change rapidly between transmit bursts, limiting the ability to create transmission signals with different amplitudes on alternate transmit bursts, a capability that is highly desirable for mixed mode operation.

Pulse generator circuits are often configured to provide signals of different magnitudes (amplitudes) to the individual elements of a transducer array. The arrangement of signal amplitudes applied to the elements of transducer arrays are often referred to as amplitude apodization profiles. Proper application of amplitude apodization reduces the magnitude of side lobes in transmitted acoustic beams. Apodization profiles are typically created using banks of pulse generating circuits powered by independent programmable d.c. voltage sources. The number of apodization levels is limited to the number of programmable d.c. voltage sources. For practical reasons, only a small number of programmable d.c. voltage sources can be provided, resulting in a piecewise approximation of the intended apodization profile.

The deficiencies of pulse generator circuits are most apparent in imaging modalities where a signal is transmitted at a fundamental frequency and images are constructed from received harmonic signals generated by non-linear acoustic propagation, so-called "harmonic imaging". Similarly, pulse generator circuits exhibit less than satisfactory results when used to image harmonic signals generated by contrast agents. The basic reason for these unsatisfactory results is that the harmonic content of signals produced by pulse generator circuits typically exceeds levels required for optimal harmonic imaging modalities. In such imaging modalities, the harmonic content of the transmitted signal effectively increases the noise floor of the received harmonic signal. For optimal performance transmitted harmonics must be suppressed.

So-called arbitrary waveform generators have been advanced as a solution to the above noted problems with pulse driven phased array transducers. Arbitrary waveform generators use stored digital representations of shaped waveforms to generate, using a digital-to-analog converter, an analog drive signal for the transducer. The drive signals produced by an arbitrary waveform generator are typically gaussian or hamming modulated cosines individually formed for each transducer element. Arbitrary waveform generators can provide instantaneous change in transmit energy between transmit pulses, apodization profiles with greater resolution, and acoustic beams with lower harmonic content.

A basic arbitrary waveform generator, used to drive ultrasonic transducer elements, is described by R. Y. Liu in "The Design of Electric Excitations for the Formation of Desired Temporal Responses of Highly Efficient Transducers," Acoustical Imaging, Vol., 12, 1982. The system described by Liu uses memory to store digitized waveform samples, a functional module to retrieve samples from memory, a digital to analog converter, and a broadband driver to excite a transducer element. In Liu's system, digitized waveform samples are pre-calculated and stored in memory.

John A. Hossack, et al., discloses the use of an arbitrary function generator to generate an excitation signal for an ultrasound transducer in "Improving the Characteristics of a Transducer Using Multiple Piezoelectric Layers," IEEE Transactions on Ultrasonics, Ferroelectrics, and Frequency Control, Vol. 40, No. 2, March 1993. The Hossack et al. ultrasonic system includes a computer that stores a digital waveform in a memory integrated circuit chip. A digital counter sequentially addresses the memory integrated circuit and data is read from the memory when addressed. Data read from the memory integrated circuit is converted by a digital-to-analog converter (DAC) and amplified to drive an ultrasound transducer.

U.S. Pat. No. 5,675,554 (Christopher R. Cole et al.) describes an arbitrary waveform generator used to drive individual elements of an ultrasonic transducer array in medical imaging applications. This implementation utilizes a digital memory to store a pre-calculated time domain transmit waveform envelope for each transmit channel. These transmit waveform envelopes are base band (near zero Hz) and may be of arbitrary shapes including variations of Gaussian and Hamming. Upon the start of a transmit event and after an appropriate focusing delay, each channel's transmit waveform envelope is retrieved from memory and sent through a dedicated signal processing path where apodization weighting and fine focus delay adjustments are applied by digital multipliers. An amplitude modulator in each digital signal processing path modulates a high frequency carrier with the channel's base band waveform envelope. The resulting digital version of the amplitude modulated transmit signal is converted by a digital to analog converter and amplified prior to driving an element of an ultrasonic transducer array.

U.S. Pat. No. 5,608,690 (Hossack et al.) and U.S. Pat. No. 5,740,128 (Hossack et al.) disclose an arbitrary waveform generator for driving individual elements of a transducer array. The described arbitrary waveform generator operates similar to that described in the earlier mentioned academic paper published by Hossack et al., "Improving the Characteristics of a Transducer Using Piezoelectric Layers." This architecture utilizes digital memory to store the actual time domain waveform samples that are sent to analog to digital converters and amplifiers so as to drive individual elements of transducer arrays. The waveforms stored in memory are digital versions of the envelope modulated drive signals sent to each ultrasound transducer element.

The arbitrary waveform generators described above have limitations. The amplitude of transmit signals generated by these implementations are controlled by adjusting the magnitude of the stored digital representation of the waveform. This requires the re-calculation and the re-storing of the waveform for each change in amplitude. Not only is this approach resource intensive, but it also results in the undesirable reduction of transmit signal resolution. To put it another way, as the amplitude of the signal being described decreases, the ability to accurately describe that signal also decreases since fewer digital bits are used to represent the signal.

Arbitrary waveform generators that adjust acoustic power by scaling the digital representation of transmit signals also increase harmonic content as acoustic power is reduced. This is because, as transmit signal resolution is reduced, the harmonic content of the transmit signal increases. While, the harmonic content can be removed from the transmit signal with high order low pass filters, such a solution is unwieldy due to the large bank of filters required for each transmit channel.

SUMMARY OF THE INVENTION

An arbitrary waveform generator that stores an optimized digital representation of a waveform in a memory and, after retrieval thereof, adjusts an amplitude of the waveform to generate an analog signal for exciting an element of an ultrasonic transducer. The arbitrary waveform generator includes an arithmetic element that accesses digitized waveform samples (or "digital waveform samples") from a waveform sample memory and adjusts the amplitude thereof. Preferably, the arithmetic element is a multiplying digital-to-analog converter (MDAC) that has a first input connection for receiving digitized waveform samples and has a second input connection for receiving a reference signal. The output signal from the MDAC is a mathematical product of the digitized waveform samples and the reference signal. A controller provides the reference signal based on a requested power level and/or an imaging modality being utilized. The optimized digital representation of the waveform may be updated as needed, for example by the controller.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
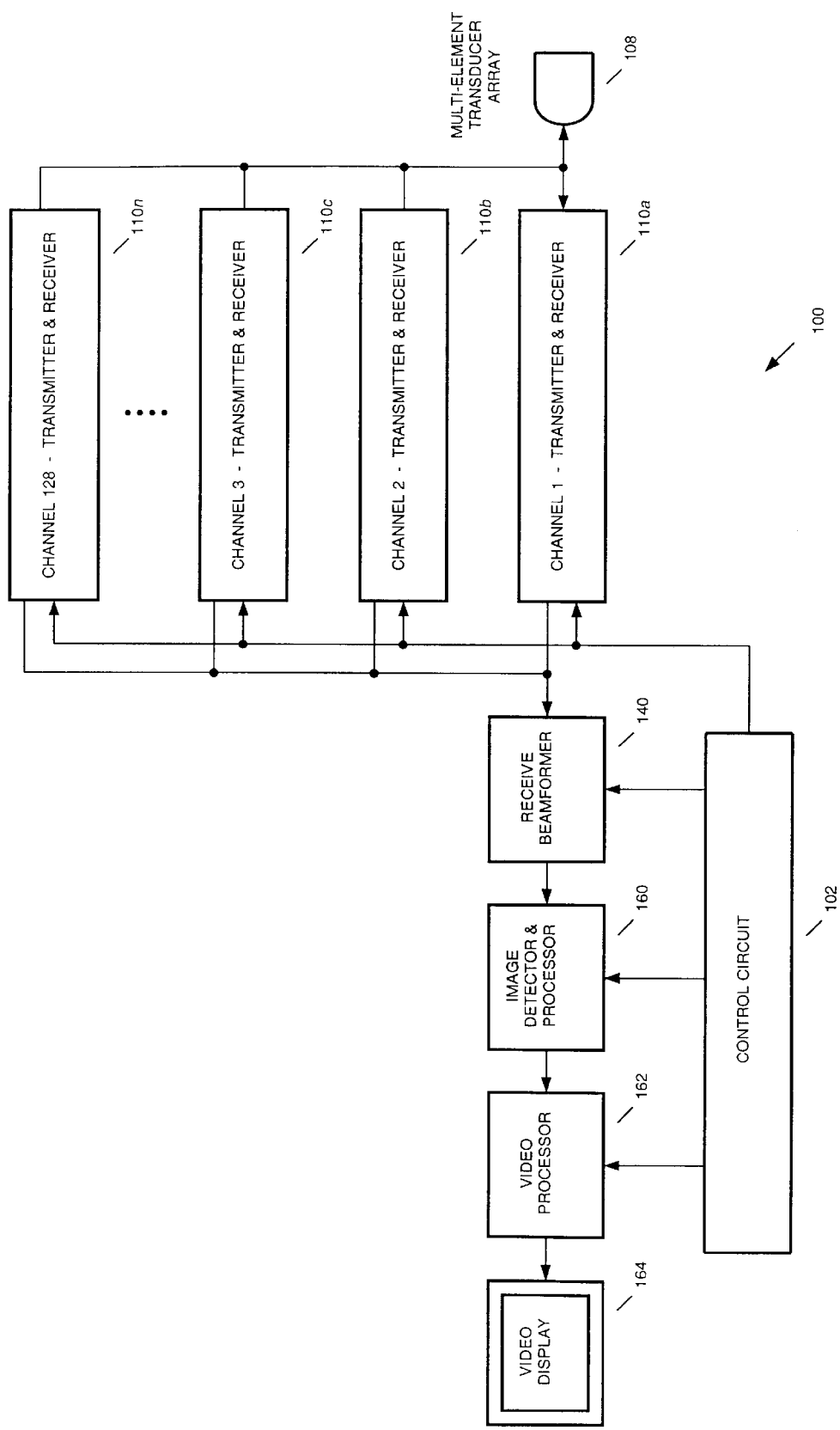
FIG. 1 is a block diagram of a multi-channel phased array ultrasound imaging system in accordance with the preferred embodiments of the present invention.

Reference will now be made in detail to the present preferred embodiments of the present invention, examples of which are illustrated in the accompanying drawings, wherein like reference numerals refer to like elements throughout.

FIG. 1 is a block diagram of a multi-channel phased array ultrasound imaging system 100 in accordance with the preferred embodiments of the present invention. It will be appreciated by those of ordinary skill in the relevant arts that the ultrasound imaging system 100, as illustrated in FIG. 1, and the operation thereof as described hereinafter is intended to be generally representative of such systems and that any particular system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

An ultrasound system 100 includes a plurality of channels 110a~110n. In the example shown, 128 channels are provided, although those of ordinary skill in the art will recognize that the number of channels may vary depending on the type of ultrasound system (for example expensive vs. inexpensive; general purpose vs. special purpose) and the type of transducer. Each Channel 110n includes a transmitter circuit and a receiver circuit. Collectively, the channels 110n drive an ultrasound transducer 108. Preferably, each channel 110n drives a single element (not shown) of the ultrasound transducer 108.

A control circuit 102 stimulates the transmitter circuit (described hereinafter with respect to FIGS. 2 and 3) of each channel 110n so as to generate an ultrasound signal from the transducer array 108. The echoes of the ultrasound signal received by the elements in the transducer array 108 are transmitted to and combined by a receive beamformer 140, in a known manner, to construct signals representing focused lines of acoustic reflection. The signals are passed from the receive beamformer 140 to an image detector and processor 160 that converts, using known techniques, the signals into a variety of useful formats. For example the image detector and processor 160 can apply techniques for amplitude detection to generate gray scale tissue images, or frequency detection to generate images of blood flow. Image data is passed to a video processor 162 that applies scan conversion to create image data in an X-Y format and subsequently converts the image data into an industry standard video format for display on a video display 164.

Figure 2:
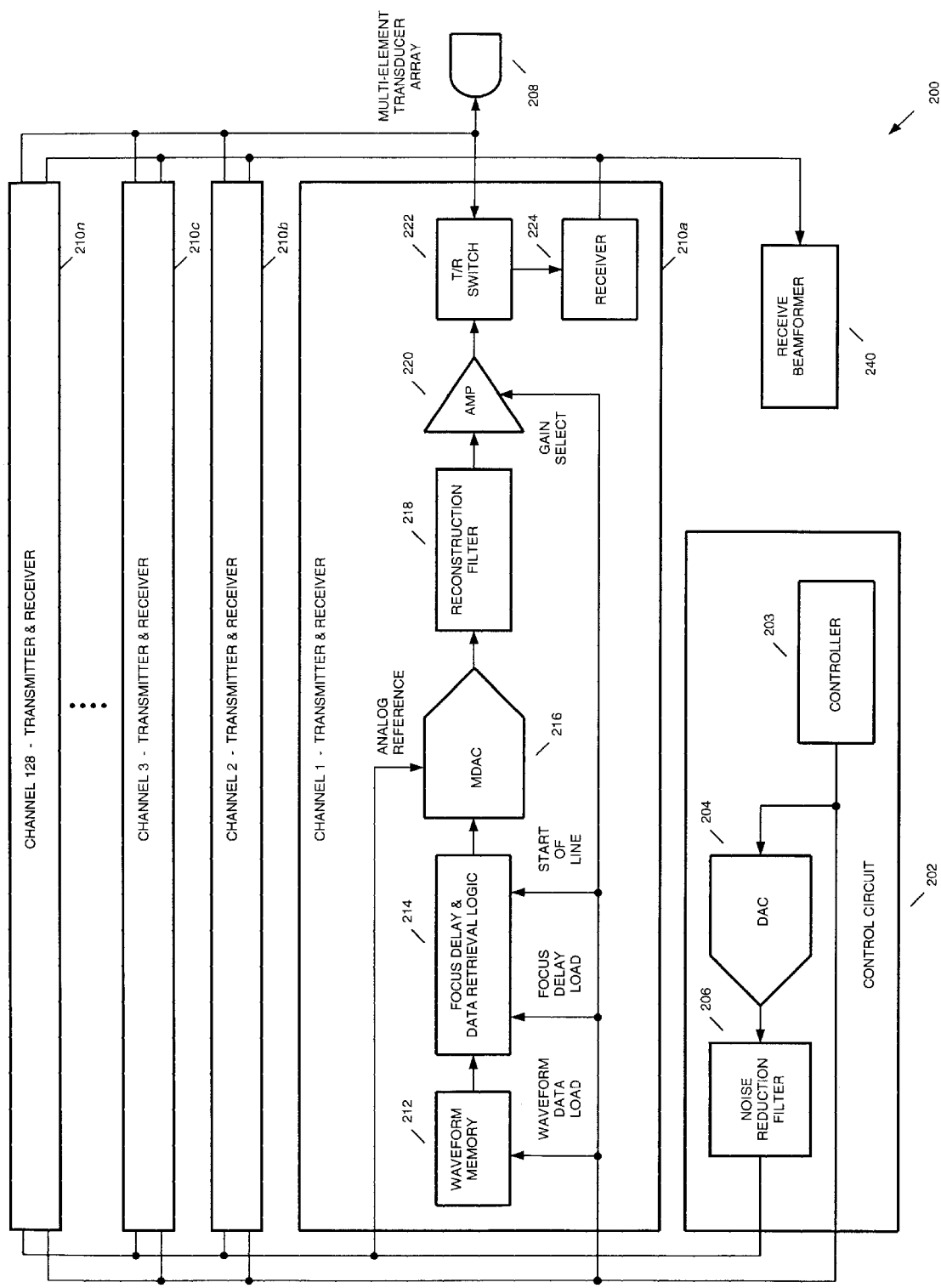
FIG. 2 is a block diagram of a multi-channel phased array ultrasound imaging system, showing one channel in detail, in accordance with a first preferred embodiment of the present invention.

FIG. 2 is a block diagram of a multi-channel phased array ultrasound imaging system 200, showing one channel 210a in detail, in accordance with a first preferred embodiment of the present invention. As with FIG. 1, it will be appreciated by those of ordinary skill in the relevant arts that the ultrasound imaging system 200 is to be regarded as illustrative and exemplary and not limiting as regards the invention described herein or the claims attached hereto.

As with the system shown in FIG. 1, a plurality of channels 210a~210n are provided. The transmitter circuits of the channels 210a~210n of the ultrasound imaging system 200 operate as arbitrary waveform generators. While only one channel 210a is depicted for purposes of simplicity of understanding, those of ordinary skill in the art will recognize that each of the remaining channels 210b–210n may have similar configurations.

A control circuit 202 drives the transmitter circuit of each channel 210n so as to drive elements (not shown) in a transducer array 208 to produce an ultrasound signal. The echoes of the ultrasound signal are received by the elements in the transducer array 208, processed by a receiver 224 in each channel and combined by a receive beamformer 240, in a known manner, to construct signal representing focused lines of acoustic reflection. The signals are subsequently processed as in FIG. 1, however certain elements are omitted here so as to concentrate on the inventive transmitter and operation thereof.

The transmitter of each channel 210n includes a waveform memory 212, a focus delay and data retrieval logic unit 214, a multiplying digital-to-analog converter 216 (hereinafter MDAC 216), a reconstruction filter 218 and an amplifier 220. A T/R switch 222 switches the operation of the transducer between transmitting and receiving in a known manner.

Generally, the MDAC 216 converts a digital representation of a waveform, stored in the waveform memory 212 in the form of digitized waveform samples (also referred to as "digitial waveform samples"), into an analog signal that is subsequently passed through the reconstruction filter 218 and amplified by the amplifier 220. The MDAC 216 receives a digital input signal and produces an analog output signal that relates to the mathematical product of the digital input signal and an analog signal applied to a reference input terminal thereof. Generally, the analog output signal from the MDAC 216 is equal, or approximately equal, to a linear function, or otherwise a function of the digital input signal and the applied reference signal. As opposed to the prior art which adjust the amplitude of the acoustic signal output by the transducer by modifying the stored digitized waveform samples, the present invention modifies the amplitude of the signal output by the transducer by multiplying the digitized waveform samples after they have been converted to an analog signal. As described below, the amplifier 220 is used to make additional modifications to the acoustic signal based on an imaging modality used.

The control circuit 202 generally comprises a controller 203, a DAC 204, and a noise reduction filter 206. The amplitude of the signal output by the MDAC 216 is controlled by the output of the DAC 204 (preferably at least a 12-bit DAC), which converts a digital signal from the controller 203 into an analog signal applied to the reference terminal of the MDAC 216. The analog signal from the DAC 204 is preferably filtered by a noise reduction filter 206 prior to being applied to the reference terminal of the MDAC 216. The noise reduction filter 206 is preferably a second-order 5 Hz, low-pass noise reduction filter that reduces low frequency spectral and 1/f noise in the range of detectable continuous-wave Doppler frequencies.

The waveform memory 212 functions as storage for a digital representation of a waveform in the form of a plurality of digitized waveform samples. Preferably, each waveform memory 212 provides at least 512 bytes of memory for storing the digitized waveform samples. The digitized waveform samples preferably have a format of seven magnitude data bits with one sign bit per sampling point (although other formats may be used). Additionally, the block of memory assigned to a channel may contain multiple digital representations of waveforms that may be independently retrieved for a particular imaging modality.

The resolution of a digital representation waveform is proportional to the number of digital codes representing the waveform's magnitude at the point of sampling. The greater the number of digital codes used to describe each digitized waveform sample, the higher the resolution of the digitized waveform sample and the overall digital representation of the waveform. The maximum number of digital codes is limited by the number of bits per sample within the waveform memory 212. In accordance with the preferred embodiment, each digitized waveform sample within the waveform memory 212 preferably comprises eight bits (seven amplitude data bits plus one sign bit) for a maximum of 256 digital codes.

An optimized digital representation of a waveform has the maximum available resolution. To optimize a digital representation of a waveform, the digitized waveform samples describing the waveform, such as those stored in waveform memory 212, are scaled by software so that their maximum peak to peak amplitude corresponds to the maximum number of available digital codes. Typically, digital representations of waveforms that have been optimized for maximum resolution are used for all modes of operation including gray scale imaging (2-D), color flow imaging, pulse Doppler imaging, and continuous wave (CW) Doppler imaging. A distinct advantage of the present invention is that optimized digital representations of waveforms are stored in waveform memory remain in an optimized state with maximum waveform resolution independent of acoustic power settings (which are controlled by setting the gain of the MDAC 216 and/or the amplifier 220). The optimized digital representations of waveforms may be further optimized to compensate for errors and distortions induced by the circuitry in the channels. The goal is to produce a digital representation of a waveform that results in an acoustic signal by the transducer with controllable harmonic content.

In operation, the controller 203 provides data and timing signals to the individual channels 210n to coordinate the generation and reception of ultrasound signals and echoes. The channel 210 is prepared for operation by the controller 203 calculating and loading digitized waveform samples describing an acoustic signal into the waveform memory 212. Next, the focus delay and data retrieval logic unit 214 retrieves data from the waveform memory 212 according to timing set by start and focus delay signals sent by the controller 203. The controller 203 may employ various known control techniques to specify timing. In any event, in accordance with a preferred mode of operation, the controller 203 conveys a trigger signal indicative of the start of a transmit event and sets a focusing delay load in the focus delay and data retrieval logic unit 214. Alternatively, other resources inside or outside the ultrasound imaging device 200 may produce the trigger and delay signals. Following the trigger event and after the focusing delay is finished, focus delay and data retrieval logic unit 214 retrieves digitized waveform samples from waveform memory 212 and conveys the samples to the MDAC 216. In accordance with the preferred embodiment, the MDAC 216 preferably receives the digitized waveform samples at a rate of 40 MHz.

The MDAC 216 outputs an analog signal based on the product of the digitized waveform samples and an analog signal from the control circuit 202 (via the DAC 204). The analog signal output by the MDAC 216 is preferably filtered by the reconstruction filter 218 to smooth or average the discrete steps of the sampled waveform. Preferably, the reconstruction filter 218 is a fourth-order, 20 MHz, low-pass reconstruction filter, although other alternatives are know to those of ordinary skill in the art. The filtered signal from the reconstruction filter 218 is sent to the amplifier 220 (preferably a linear amp) that drives an element of the ultrasonic transducer 208. The gain of the amplifier 220 is controlled by the controller 203. Alternatively, a gain control signal may be supplied from sources other than the controller 203.

The gain settings of the amplifier 220 are preferably varied between at least two gain settings by a gain select signal issued by the controller 202. During transmission of signals for tissue harmonic imaging, two-dimensional imaging, color flow imaging, and other applications that utilize relatively large-amplitude transmit waveforms, the amplifier 220 is preferably set to a high gain setting to drive the large amplitude signals to the transducer. In contrast, for low amplitude waveform signal applications such as continuous-wave Doppler data acquisition, a low gain setting is preferable so as to increase the signal-to-noise ratio of the electrical signal driving the transducer. Transmit signals for continuous-wave Doppler are significantly lower in amplitude than signals in other operating modes. With the amplifier 220 set for high gain, the spectral noise contributed by the MDAC 216 is unacceptable for continuous-wave Doppler mode operation. Accordingly, the gain of the linear amplifier 220 is preferably reduced so that the noise contributed by the MDAC 216 is significantly reduced, resulting in a transmit waveform with an improved signal-to-noise ratio and a lower continuous-wave Doppler noise floor.

Under typical operating conditions, the controller 203 scales the magnitude of the digitized waveform samples in the waveform memory 212 to maximize digital resolution. The controller 203 then adjusts acoustic power simply by changing the setting of the DAC 204. During normal operation, the samples in the waveform memory 212 remain constant. Such arrangement reduces the formatting time for power changes since new digitized waveform samples do not need to be calculated and loaded into waveform memory 212. In addition, the resolution of the digital representation of the waveform remains optimal for all power settings. The gain setting of the amplifier 220 also affects acoustic power, e.g. as the gain of the linear amplifier 220 changes, the scale factor relating the digital input signal to the acoustic power of the output signal also changes. Control logic, such as control functions implemented in system software, may track the gain of the amplifier 220 and adjusts the scale factor of the DAC 204 accordingly.

It will be appreciated by those skilled in the art that changes may be made in the first embodiment without departing from the principles and spirit of the invention, the scope of which is defined in the claims and their equivalents. The illustrative ultrasound imaging system 200 has a controller 202, DAC 204, and noise reduction filter 206. However, those of ordinary skill in the art will recognize that one or more central controllers may be used. The amplitude control DAC 204 is optional and may be excluded from a particular example of a ultrasound imaging device 200. Alternatively, some ultrasound imaging devices may include one or more amplitude control DACs. Furthermore, the noise reduction filter 206 is optional and may be excluded from a particular example of a ultrasound imaging device 200. An ultrasound device with multiple amplitude control DACs may have a noise reduction filter connected to the output line from each amplitude control DAC. Alternatively, a plurality of noise reduction filters may be cascaded at the output line of the amplitude control DAC to effectively operate as a single filter. Additionally, the acoustic power setting operation may be executed by logic other than the controller 203. For example, the acoustic power may be set by dedicated logic within the ultrasound imaging device 200, by logic external to the ultrasound imaging device 200, or by other suitable logic. The MDAC 216 could also be replaced by a DAC and a separate, subsequent, analog multiplier.

Figure 3:
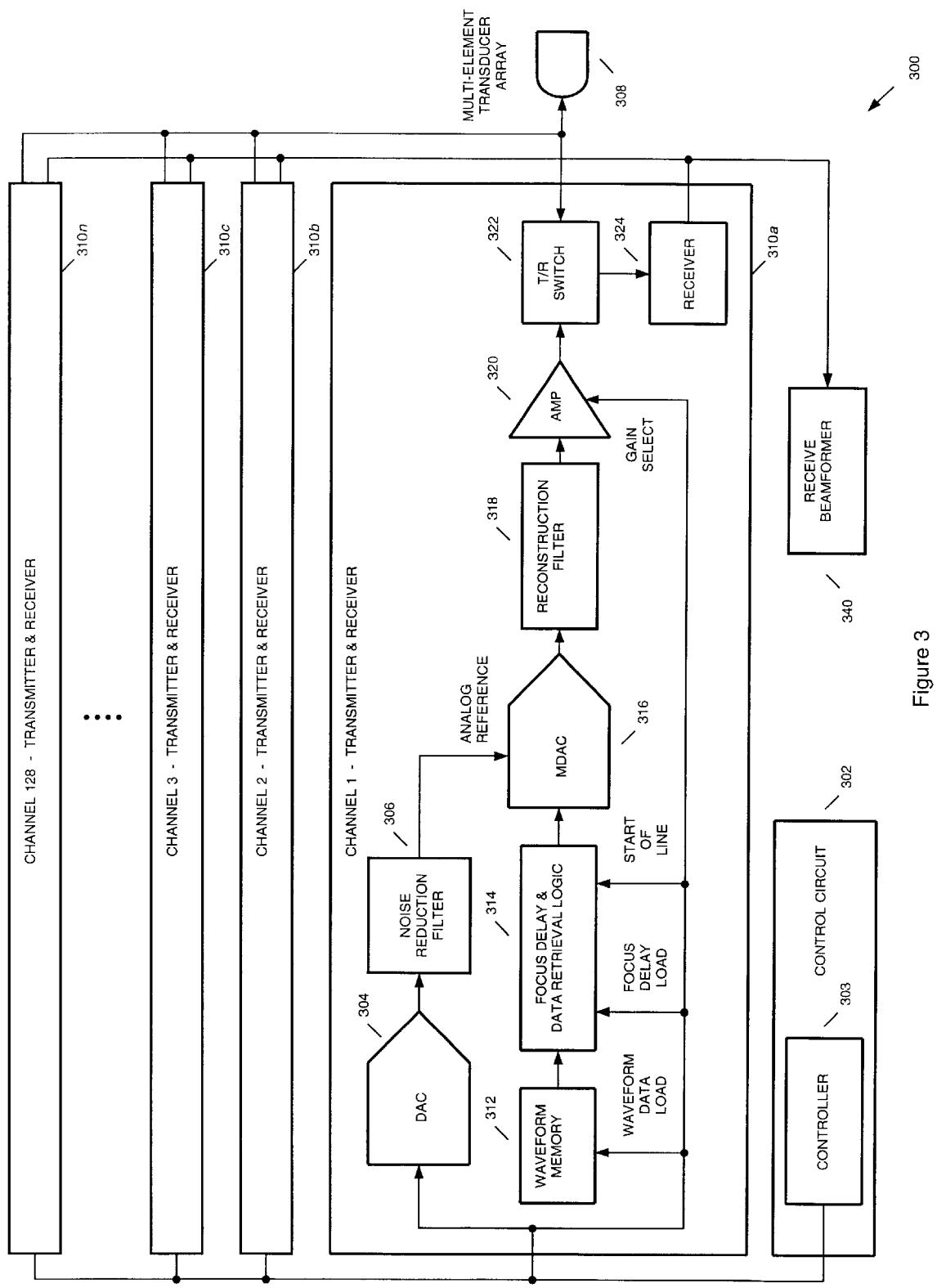
FIG. 3 is a block diagram of a multi-channel phased array ultrasound imaging system, showing one channel in detail, in accordance with a second preferred embodiment of the present invention.

FIG. 3 is a block diagram of a multi-channel phased array ultrasound imaging system 300, showing one channel in detail, in accordance with a second preferred embodiment of the present invention. The ultrasound imaging system 300 shown in FIG. 3 is similar to the ultrasound imaging system 200 shown in FIG. 2, with the modification that a DAC 304 and associated noise reduction filter 306 are provided for each transmit circuit in each channel 31 On, as opposed to the use of a central DAC 204 and noise reduction filter 206, as shown in FIG. 2. In this configuration, a control circuit 302 comprises a controller 303. As described above, a receive beamformer 340 is provided to combine received echoes. Thus, each channel 310n has a transmitter that drives an element (not shown) of a transducer array 308. The transmitter is provided with a waveform memory 312, a focus delay and data retrieval logic 314, a MDAC 316, a reconstruction filter 318, and an amplifier 320, along with the aforementioned DAC 304 and associated noise reduction filter 306. Each channel 310n also has a transmit/receive switch 322 and a receiver 324.

Those of ordinary skill in the art will recognize that modifications described above with respect to the ultrasound system 200 can be made to the ultrasound system 300.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the structures necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A transmitter circuit for a transducer in an ultrasound system, the transmitter circuit comprising:

an arithmetic unit that converts a digital representation of a waveform to be produced by the transducer into an analog signal and multiplies the analog signal by a gain factor to generate a gained signal which determines characteristics of a subsequent output signal produced by the transducer; and a control circuit that modifies the gain factor to adjust an amplitude of the signal produced by the transducer.

2. A transmitter circuit according to claim 1 wherein the arithmetic unit includes a multiplying digital-to-analog converter.

3. A transmitter circuit according to claim 2 wherein:

the multiplying digital-to-analog converter is at least an 8-bit multiplying digital-to-analog converter.

4. A transmitter circuit according to claim 2 wherein:

the multiplying digital-to-analog converter is at least a 10-bit multiplying digital-to-analog converter.

5. A transmitter circuit according to claim 2 wherein:

the multiplying digital-to-analog converter is at least a 12-bit multiplying digital-to-analog converter.

6. A transmitter circuit according to claim 2 wherein:

the multiplying digital-to-analog converter is at least a 14-bit multiplying digital-to-analog converter.

7. A transmitter circuit according to claim 1 further comprising:

an amplifier that amplifies the output of the arithmetic unit with a gain to minimize spectral noise of the transmit signal for CW Doppler imaging.

8. A transmitter circuit according to claim 1 wherein the arithmetic unit includes:

a digital-to-analog converter; and an analog multiplier that communicates with the digital-to-analog converter.

9. A transmitter circuit according to claim 8 wherein:

the digital-to-analog converter is at least an 8-bit digital-to-analog converter.

10. A transmitter circuit according to claim 1 further comprising:

an amplifier that receives the gained signal, amplifies the gained signal based on a gain control signal to generate an amplified signal, and supplies the amplified signal to the transducer.

11. A transmitter circuit according to claim 10 wherein:

the control circuit modifies the gain control signal to improve signal-to-noise ratio.

12. A transmitter circuit according to claim 10 further comprising:

a reconstruction filter connected between the arithmetic unit and the amplifier, the reconstruction filter that smoothes the gained signal.

13. A transmitter circuit according to claim 1 wherein the control circuit includes:

a central controller that generates a digital gain factor; and a digital-to-analog converter that converts the digital gain factor into a gain factor for usage by the arithmetic unit.

14. A transmitter circuit according to claim 13 wherein the control circuit further includes:

a noise reduction filter that filters an output signal from the digital-to-analog converter.

15. A transmitter circuit according to claim 1 further comprising:

a waveform memory that stores an optimized digital representation of the waveform; and a data retrieval circuit that retrieves the optimized digital representation of the waveform from the waveform memory and supplies the optimized digital representation of the waveform to the arithmetic unit as the digital signal.

16. A transmitter circuit according to claim 15 wherein:

the optimized digital representation of the waveform is comprised of a plurality of digitized waveform samples.

17. A transmitter circuit according to claim 15 wherein:

the optimized digital representation of the waveform is optimized to cause the transducer to produce a waveform with controllable harmonic content regardless of the acoustic power produced by the transducer.

18. A transmitter circuit according to claim 15 wherein:

the data retrieval circuit retrieves the optimized digital representation of the waveform at a timing determined by the control circuit.

19. A transmitter circuit according to claim 15 wherein:

the control circuit generates the optimized digital representation of the waveform.

20. A transmitter circuit according to claim 15 wherein:

the control circuit optimizes the digital representation of the waveform to produce a waveform having controllable harmonic content.

21. A transmitter circuit according to claim 7 wherein:

the control circuit controls the gain of the amplifier based on the use of CW Doppler imaging.

22. A transmitter circuit for a transducer in an ultrasound system, the transmitter circuit comprising:

a plurality of channels, one or more of the plurality of channels having an arithmetic unit that converts a digital signal representation of a waveform to be produced by the transducer into an analog signal and multiplies the analog signal by a gain factor to generate a gained signal which determines characteristics of a subsequent output signal produced by the transducer;

a controller that generates a digital gain factor; and a digital-to-analog converter that converts the digital gain factor into a gain factor for the arithmetic unit.

23. A transmitter circuit for a transducer in an ultrasound system, the transmitter circuit comprising:

a plurality of channels, one or more of the plurality of channels comprising:

an arithmetic unit that converts a digital signal representation of a waveform to be produced by the transducer into an analog signal and multiplies the analog signal by a gain factor to generate a gained signal which determines characteristics of a subsequent output signal produced by the transducer; and a digital-to-analog converter that converts a digital gain factor into a gain factor for the arithmetic unit; and a controller that generates the digital gain factor for one or more of the plurality of channels.

24. A transmitter circuit for a transducer in an ultrasound system, the transmitter circuit comprising:

a memory that stores a digital representation of a waveform to be produced by the transducer, the digital waveform representation being scaled to optimize resolution;

a multiplying digital-to-analog converter that receives the digital waveform representation from the memory and multiplies the digital waveform representation by a gain factor to generate an analog signal which determines characteristics of a subsequent output signal produced by the transducer; and a control circuit that supplies the gain factor to the multiplying digital-to-analog converter so that the subsequent output signal produced by the transducer contains controllable harmonic content regardless of the acoustic power generated by the transducer.

25. A method of forming a wave signal for production by a transducer in an ultrasound system, the method comprising:

storing in a memory a digital representation of a waveform to be produced by the transducer, the digital waveform representation being optimized to maintain digital resolution;

applying the digital waveform representation to a multiplying digital-to-analog converter; and supplying a gain factor to the multiplying digital-to-analog converter to scale the amplitude of a subsequent output signal produced by the transducer.

26. A method of forming a wave signal for production by a transducer in an ultrasound system, the method comprising:

applying a digital representation of the wave signal to a multiplying digital-to-analog converter; and supplying a gain factor to a multiplying digital-to-analog converter to adjust the amplitude of a signal output by the transducer.

27. A method of forming an acoustic signal for output by a transducer in an ultrasound system, the method comprising:

generating a reduced scale digital representation of the acoustic signal by scaling a desired generated waveform of the multiplying digital-to-analog converter to optimize digital resolution;

storing in a memory the digital representation;

applying the digital waveform representation to the multiplying digital-to-analog converter; and multiplying, in the analog domain, an output signal generated by the digital-to-analog converter by a gain factor based on a desired acoustic power to be generated by the transducer, thereby forming an analog signal which determines characteristics of a subsequent acoustic signal output by the transducer.

* * * * *